(12) United States Patent
Raupp

(10) Patent No.: US 6,930,463 B2
(45) Date of Patent: Aug. 16, 2005

(54) CONTAINER INSPECTION MACHINE

(75) Inventor: Henry F. Raupp, Freeville, NY (US)

(73) Assignee: Emhart Glass S.A., Cham (CH)

( * ) Notice: Subject to any disclaimer, the term of this patent is extended or adjusted under 35 U.S.C. 154(b) by 242 days.

(21) Appl. No.: 10/610,061

(22) Filed: Jun. 30, 2003

(65) Prior Publication Data
US 2004/0263098 A1 Dec. 30, 2004

(51) Int. Cl.$^7$ .............................................. G05B 19/40
(52) U.S. Cl. ........................ 318/685; 318/696; 318/569; 318/567
(58) Field of Search ................................ 318/685, 696, 318/49, 587, 139, 569, 567, 560

(56) References Cited

U.S. PATENT DOCUMENTS 5,938,196 A * 8/1999 Antoja .................... 273/143 C
6,348,774 B1 * 2/2002 Andresen et al. ........... 318/685

* cited by examiner

Primary Examiner—Karen Masih
(74) Attorney, Agent, or Firm—Spencer T. Smith

(57) ABSTRACT

A motor controller system for operating a plurality of step motors. The step motors are arranged in a number of motor groups each having no more than "N" step motors. A group multiplexer will deliver feed signals to the correct numbered motor of a motor group. There is a single 1 axis motor control and an output drive for each motor number of a group. The 1 axis motor control supplies the group multiplexer with motor group data so that the group multiplexer will supply the correct motor group and the 1 axis motor control also individually enables the motors of that group which are to be operated and conjointly supplies all the output drives with a desired feed signal.

4 Claims, 3 Drawing Sheets

FIG. 3

|          | Motor Group #1 | Motor Group #2 | Motor Group #3 |
|----------|----------------|----------------|----------------|
| Motor #1 | • Upper Front Belt Drive | • Upper Belt Drives Up/Down Assembly | • Camera #1 Up/Down Assembly |
| Motor #2 | • Upper Rear Belt Drive | • Upper Belt Drives Up/Down Assembly | • Camera #2 Up/Down Assembly |
| Motor #3 | • Lower Front Belt Drive | • Upper Belt Drives Up/Down Assembly | • Camera #3 Up/Down Assembly |
| Motor #4 | • Lower Rear Belt Drive | • Lower Belt Drives Up/Down Assembly | • Camera #4 Up/Down Assembly |

CONTAINER INSPECTION MACHINE

The present invention relates to machines which inspect bottles for defects.

BACKGROUND OF THE INVENTION

A state of the art glass bottle inspection machine transports a line of the bottles through a number of inspection stations.

In such machines electronic motors may be used to drive any number of axes. As the number of electronic motors increase so too does the cost of controlling these motors.

OBJECT OF THE INVENTION

It is accordingly an object of the present invention to provide a control for a large number of electronic motors which has a low cost.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE DRAWINGS

FIG. 3 illustrates the motor groups for this inspection machine.

BRIEF DESCRIPTION OF THE PREFERRED EMBODIMENT

Figure 1:
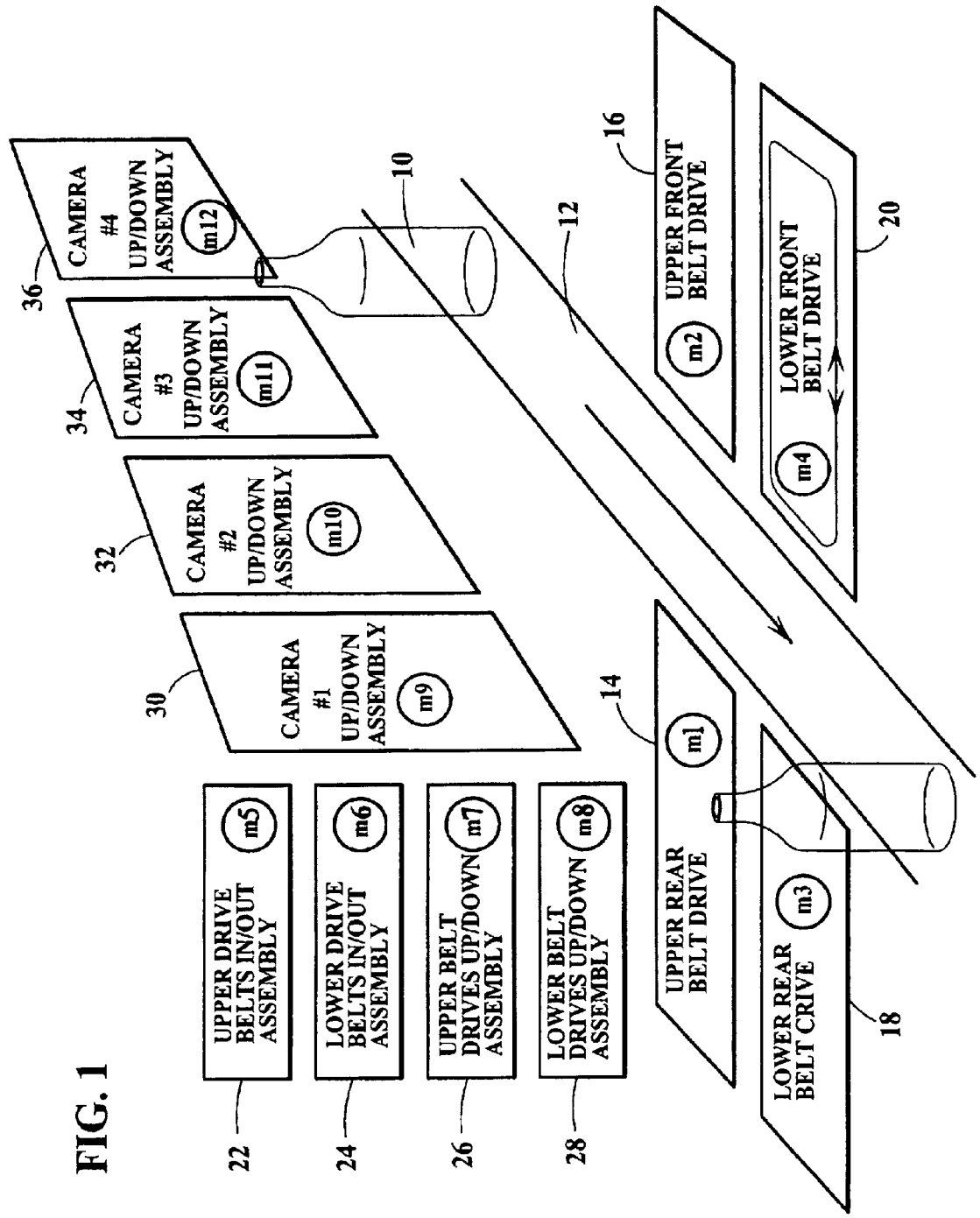
FIG. 1 is a schematic view of an inspection machine for inspecting bottles.

In the machine for inspecting bottles shown in FIG. 1, bottles 10 are transported through the machine along a conveyor path 12. In the illustrated embodiment, a portion of this displacement will be via a belt drive assembly which captures a bottle at a pick up location and conveys the bottle to a release position. Delivering the bottles to the belt drive assembly could be a horizontal conveyor and removing the bottles released from the belt drive assembly could also be a horizontal conveyor. The belt drive assembly is shown to include an Upper Rear Belt Drive 14 which would include a belt driven by a step motor M1, an opposed Upper Front Belt Drive 16 which would include a belt driven by a step motor M2, a Lower Rear Belt Drive 18 which would include a belt driven by a step motor M3, and an opposed Lower Front Belt Drive 20 which would include a belt driven by a step motor M4.

The upper drive belts and the lower drive belts are interconnected so that they can be horizontally displaced relative to one another to open or close the upper or lower belts (Upper Drive Belts In/Out Assembly 22, Lower Drive Belts In/Out Assembly 24). Each of these assemblies has its own step motor M5, M6. And both upper belt drives and both lower belt drives can be raised or lowered (Upper Belt Drives Up/Down Assembly 26, Lower Belt Drives Up/Down Assembly 28). Each of these assemblies has a step motor M7, M8.

As the belt drive assembly transports a bottle, a number of inspections will be conducted via camera based systems. In FIG. 1, four inspections are carried out with four cameras which are mounted for displacement carried out by a step motor (Camera #1 Up/Down Assembly 30, Camera #2 Up/Down Assembly 32, Camera #3 Up/Down Assembly 34, and Camera #4 Up/Down Assembly 36). Each of these assemblies has a step motor (M9, M10, M11, M12).

Figure 2:
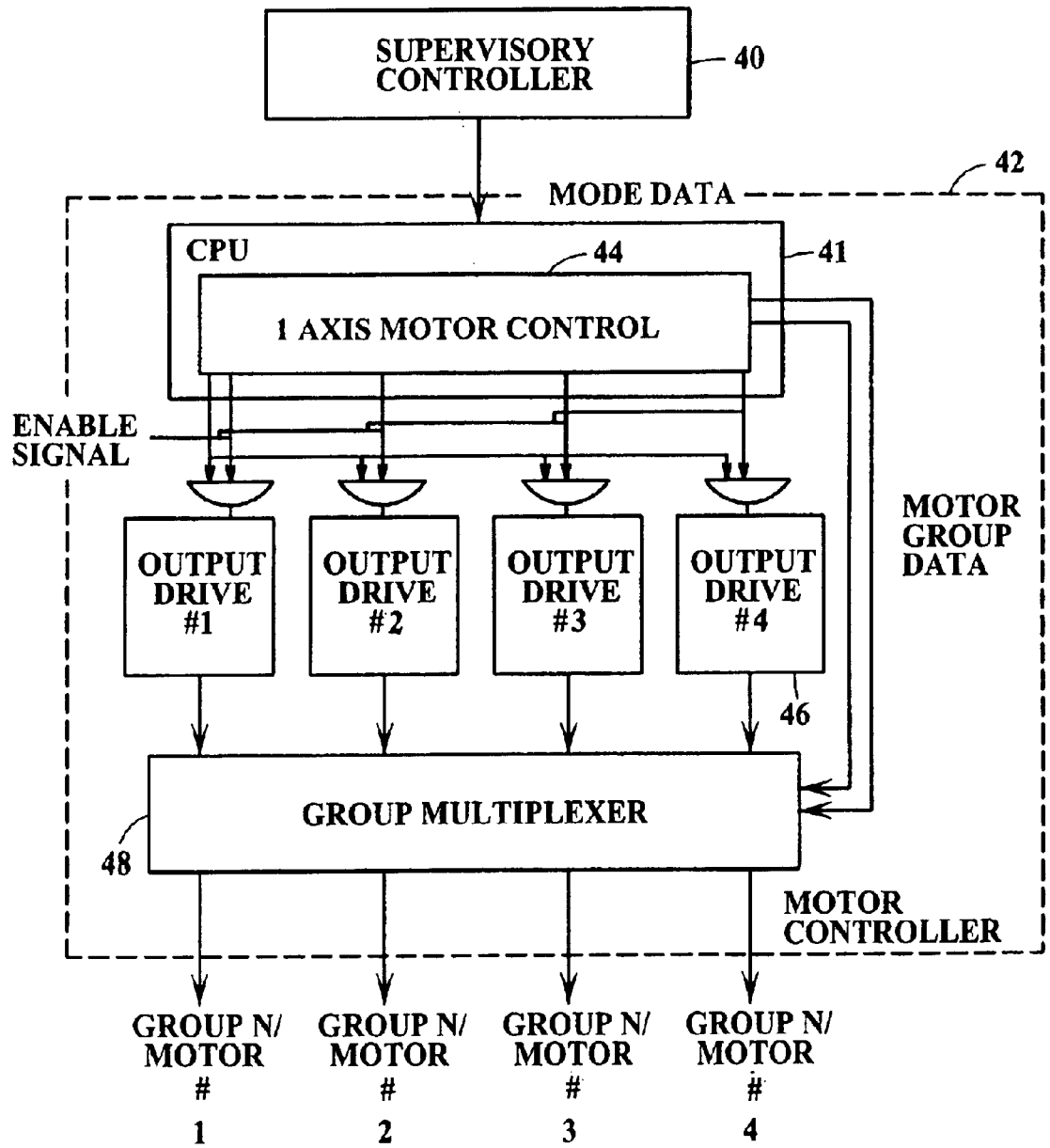
FIG. 2 is an electronic diagram of the motor control architecture.

Referring to FIG. 2, a Supervisory Controller 40 provides the CPU 41 of the Motor Controller 42 with Mode Data concerning the operation of the motors. For example the Mode Data could be for the CPU to elevate the upper belt drives, for example. The CPU includes a 1 Axis Motor Control 44 which communicates with four output drives 46 (Output Drive #1, Output Drive #2, Output Drive #3, Output Drive #4) and a Group Multiplexer 48. The CPU receives the Mode Data (run the four belt drives at full speed for example) and determines that all four belt drive step motors have to be supplied X pulses in accordance with a set feed program.

The 1 Axis Controller 44 provides Motor Group Data to the Group Multiplexer 48 to identify the motor group that is to be operated. FIG. 3 shows that in the preferred embodiment, there are three groups each having four motors (Motor Group #1, Motor Group #2, Motor Group #3). There can be any number of groups of up to four motors each and it is not necessary that each group have a full complement of four motors. As shown in FIG. 3, there is a motor matrix of four motors per group. In Motor Group #1, Motor #1 is the Upper Front Belt Drive, Motor #2 is the Upper Rear Belt Drive, Motor #3 is the Lower Front Belt Drive, and Motor #4 is the Lower Rear Belt Drive. In Motor Group #2, Motor #1 is the Upper Belt Drives Up/Down Assembly, Motor #2 is the Lower Belt Drives Up/Down Assembly, Motor #3 is the Upper Belt Drives In/Out Assembly, and Motor #4 is the Lower Belt Drives In/Out Assembly. In Motor Group #3, Motor #1 is the Camera #1 Up/Down Assembly, Motor #2 is the Camera #2 Up/Down Assembly, Motor #3 is the Camera #3 Up/Down Assembly, and Motor #4 is the Camera #4 Up/Down Assembly.

To carry out the instructions of the CPU to run the four belt drive motors at full speed, the 1 Axis Controller instructs the Group Multiplexer 48 that Motor Group #1 is to operate. This means that the output of Output Drive #1 will be directed to the Upper Front Belt Drive to operate Motor M2. The 1 Axis Motor Control also provides enable signals to each of the four Output Drives and simultaneously supplies each these motor drives with pulses at the desired frequency to run the four drive belt step motors at full speed. At the conclusion of a desired operation, the 1 Axis Motor Control 44 removes the enabled signals from each of the four output drives. In another illustration, the Supervisory Controller will supply Mode Data to the 1 Axis Motor Control to operate Motor M9 at a rapid rate. The 1 Axis Motor Control will instruct the Group Multiplexer to operate Motor Group #3. It will also enable only Output Drive #1 and supply a predetermined number of pulses in accordance with a set feed program. Whether 1, 2, 3 or 4 Output Drives are enabled the number of pulses supplied and the feed program for all enabled Output Drives will be the same.

What is claimed is:

1. A motor controller system comprising
   a predetermined number of step motors grouped in N groups with each of the N groups having no more than the selected plurality of step motors, and
   a motor controller including
      a selected plurality of output drives,
      a group multiplexer for receiving the output of said selected plurality of output drives and for supplying the predetermined number of feed programs to a corresponding step motor of a plurality of groups of step motors each having no more than the predetermined number of step motors, and processor means for individually enabling any of the selected plurality of output drives, for conjointly supplying a feed program to each of the plurality of output drives, and for supplying said group multiplexer with motor group data defining the Nth motor group to be operated.

2. A motor controller system according to claim 1, wherein said processor means comprises a 1 axis controller for individually enabling any of the selected plurality of output drives, for conjointly supplying a feed program to each of the plurality of output drives, and for supplying said group multiplexer with motor group data defining the Nth motor group to be operated.

3. A motor controller system according to claim 2, further comprising a supervisory controller for supplying mode data to said processor means.

4. A motor controller system according to claim 3, wherein said processor means is a CPU.

* * * * *